(12) United States Patent
Paris-Jolly et al.

(10) Patent No.: US 7,758,952 B2
(45) Date of Patent: Jul. 20, 2010

(54) REINFORCED STERILISING PACKAGING MATERIAL AND PACKAGING COUNTERING SAID MATERIAL

(75) Inventors: Agnes Paris-Jolly, La Mureite (FR); Christophe Simon, Maureillas las Illas (FR)

(73) Assignee: ARJOWIGGINS, Issy les Moulineaux (FR)

( * ) Notice: Subject to any disclaimer, the term of this patent is extended or adjusted under 35 U.S.C. 154(b) by 244 days.

(21) Appl. No.: 11/629,818

(22) PCT Filed: Jul. 1, 2005

(86) PCT No.: PCT/FR2005/001678
§ 371 (c)(1),
(2), (4) Date: Mar. 9, 2007

(87) PCT Pub. No.: WO2006/013255
PCT Pub. Date: Feb. 9, 2006

(65) Prior Publication Data
US 2007/0246377 A1    Oct. 25, 2007

(30) Foreign Application Priority Data
Jul. 2, 2004  (FR) .................................. 04 07343

(51) Int. Cl.
B29D 22/00 (2006.01)
D04H 1/00 (2006.01)
(52) U.S. Cl. ................................... 428/292.1; 428/35.2
(58) Field of Classification Search ............. 428/292.1; 206/10, 329, 363
See application file for complete search history.

(56) References Cited

U.S. PATENT DOCUMENTS 5,730,530 A     3/1998   Stoddard et al.
6,808,691 B1 *  10/2004  Herve et al. .................. 422/294

FOREIGN PATENT DOCUMENTS

WO   WO-96/16562 A1   6/1996
WO   WO-00/21745 A1   4/2000

* cited by examiner

Primary Examiner—D. Lawrence Tarazano
Assistant Examiner—Camie S Thompson
(74) Attorney, Agent, or Firm—Birch, Stewart, Kolasch & Birch, LLP

(57) ABSTRACT

The invention relates to a sterilizing packaging material for sterilizable medical devices, which is embodied in the form of a fibrous film containing polyamide fibers, wherein the basis weight of the film is less than 100 g/m$^2$, a mean resistance to a tear propagation is equal to or greater than 1900 mN an a bacterial filtering efficiency BFE is equal or greater than 95%. A sterilizing packaging containing said material is also disclosed.

22 Claims, No Drawings

REINFORCED STERILISING PACKAGING MATERIAL AND PACKAGING COUNTERING SAID MATERIAL

The present invention relates to a sterilization packaging material for medical devices that have to be sterilized and to the sterilization packaging itself.

Sterilization packaging for medical devices that have to be sterilized, especially instruments or reusable equipment, such as for example probes, scalpels, tongs, scissors, needles, is already known.

Such packaging is then in the form of a sachet, pouch, tube or blister pack, or else in the form of rigid packaging. The materials for this packaging are sheets based on only cellulose fibers (with no synthetic fibers) which are manufactured and sold in Europe by the company ARJOWIGGINS under the trademarks ETHYPEL® and PROPYPEL® or ARJOPEEL™. These sheets have a high bacterial barrier but a mechanical strength which may prove insufficient even if they have been surface-treated by a reinforcing agent such as starch, polyvinyl alcohol or an acrylic latex when it is desired to package heavy or blunt objects.

This packaging may also be in the form of sheets that can be folded around objects or devices to be sterilized, such as reusable surgical equipment, for example an orthopedic kit. This packaging consists of flexible paper sheets or nonwovens which allow said equipment to be sterilized and ensure that it is kept in the sterile state right up to the moment of the surgical operation, for which the sheet is unfolded, it being possible to carry out the unfolding either in an airlock before entering the operating theater, or only in the operating theatre. These sheets may be paper sheets reinforced by synthetic fibers mixed with cellulose fibers. For example, such sheets comprising polyester synthetic fibers are sold by ARJOWIGGINS under the brand name STERISHEET®. For an equivalent grammage, these reinforced sheets have a higher mechanical strength than purely cellulose sheets but, on the other hand, their bacterial barrier is slightly lower.

Rigid packaging generally consists of a thermoformed plastic container that will contain the medical products to be sterilized and which will then be closed by a cover, which may be a paper sheet acting as a barrier to microorganisms and able to be sealed.

Flexible or semirigid packaging in the form of a sachet, pouch, tube or blister pack is a packaging formed from a part which may be made from synthetic material and from paper or nonwoven sheet having a specific permeability, these being sealed to each other over a certain perimeter depending on the desired shape of the packaging, a relatively large opening being left so as to be able to introduce the objects.

The objects to be sterilized are placed inside the packaging and then said packaging is completely sealed. The part made of synthetic material may be a thermoplastic film such as polyethylene or polypropylene film. This film is in general impermeable to gases and to water vapor and, in addition, is transparent so that the contents of the packaging may be seen. Instead of the plastic film, it is also possible to use a sheet similar to a sheet of paper having a specific permeability or a sheet of paper coated with a sealant such as a layer of extruded polyethylene or polyvinyl acetate.

In the case of a blister pack, a flexible plastic film thermoformed to the shape of the device to be packaged is used.

The sheet used in such rigid or flexible packaging must have a specific permeability that makes it a barrier to microorganisms but allows sterilizing agents to pass through it so as to sterilize the closed packaging and its contents by sterilization methods using, as sterilizing agents, steam or sterilizing gases such as ethylene oxide or formaldehyde. The packaging may also be sterilized by ionizing radiation, such as gamma-radiation or beta-radiation.

Patent Application WO 00/21745 has proposed a material having mechanical characteristics and microorganism barrier properties that are relatively high. This material consists of at least two sheets of sterilization packaging bonded together via one of their faces in a nonreversible manner, especially by lamination. However, the design of this sterilization packaging still has a few drawbacks.

Firstly, production of the material itself requires a relatively heavy and complex manufacturing process, as well as an additional consumption of sealants.

This consequently results in a manufacturing cost that is still too high and leads to a material of relatively high grammage, going counter to the recommendations according to directive 2004/CE/12 of the European Union with regard to packaging and packaging waste, which recommend a reduction in the weight of packaging.

Secondly, certain properties of the sterilization packaging obtained according to patent WO 00/21745 may be considered insufficient with regard to very specific medical applications.

In particular, one of the desired properties is that the sheet be tear-resistant. This is because, since it is intended to form packaging that may contain possibly heavy or blunt objects it runs the risk of being torn or transpierced by these objects when said packaging is being handled. In the case of sealable sterilization packaging, the aim is to obtain a mean initial tear strength of greater than 300 mN (measured according to the European Standard EN 21974). However, in certain applications it is preferable for this initial tear strength to be much higher, at least 1900 mN (measured according to European Standard EN 21974).

Another desirable property is that the sheet constitutes an effective barrier to bacteria or other microorganisms in order to maintain the sterility of the packaging, that is to say microorganisms must not be able to penetrate into the packaging after sterilization. It is therefore necessary for the mean of the largest pore diameters not to be too large and for no pores to have an excessively large diameter. This barrier property may be characterized by the bacterial filtration efficiency usually referred to the initials of its English term BFE (bacterial filtration efficiency); it is expressed as a percentage, which represents the percentage number of bacteria stopped by the sheet. In the case of sealable sterilization packaging, it is desirable to have a BFE of at least 85%.

However, it is not uncommon to require, in certain types of packaging, a much higher level of bacterial protection, especially packaging having a BFE of at least 95%.

Hitherto, the coexistence of these two properties at high levels within the same packaging has proved difficult.

This is because, in the prior art, the solutions adopted always correspond to a compromise between the desire for good mechanical strength, especially tear strength, and a good barrier effect to bacteria or other microorganisms. To obtain a high value for one of these properties then results in a relatively low value for the other of these properties.

Consequently, it turns out that the sterilization packagings currently available on the market do not always meet the requirements of users in this field, nor the European Union Directives recommending a reduction in the weight of packagings.

The object of the present invention is therefore to provide a sterilization packaging material that has high levels both as regards its initial tear strength and its microorganism barrier effect, whilst still having the lowest possible grammage.

The Applicant has found that, with polyamide-type synthetic fibers incorporated into fiber structures, a material that solves the stated problem is obtained.

The invention thus provides a sterilization packaging material for medical devices that have to sterilized, characterized in that it is in the form of a fibrous sheet comprising polyamide (PA) fibers, said sheet having a grammage of less than 100 g/m$^2$, measured according to international standard ISO 536, a mean initial tear strength, measured according to European Standard EN 21974, of 1900 mN or higher and a bacterial filtration efficiency BFE of 95% or higher.

The sheet may be formed from a single layer of fibers (monolayer or single-ply sheet) or from several layers of fibers (multilayer or multi-ply sheet).

The term "mean strength" is understood to mean the arithmetic mean of the strength measurement made along a first direction of the sheet and of the strength measurement made along the direction perpendicular to this first direction. This first direction corresponds to a preferred orientation of the fibers, when there is one such orientation, generally this being the direction of orientation of the fibers along their length direction; this direction corresponds to the machine direction of the machine used to manufacture the sheet, the perpendicular direction therefore corresponding to the direction transverse to the machine direction. If the fibers do not have a preferred orientation, measurements along two perpendicular directions are made.

Preferably, said sheet has a grammage of 90 g/m$^2$ or less, preferably comprised between 40 and 80 g/m$^2$, measured according to the international standard ISO 536.

According to one particular embodiment of the invention, the polyamide fibers are chosen from polyamide-6, polyamide-6,6, polyamide-6,9 and polyamide-6,10 fibers and mixtures thereof. Preferably, the polyamide fibers are polyamide-6,6 fibers. These fibers may be of bi-component type.

Also preferably, said polyamide fibers have a length of 5 mm or greater. For example, their length may be comprised between 5 and 25 mm.

Also preferably, said polyamide fibers have a mean linear density of greater than 1.5 dtex.

According to one particular embodiment of the invention, said polyamide fibers are chopped fibers. According to another particular embodiment of the invention, said polyamide fibers are continuous fibers (filaments).

Preferably, said polyamide fibers include antioxidants in order to give them irradiation resistance.

According to one particular embodiment of the invention, said fibrous composition includes, in the bulk, refined cellulose fibers, preferably refined to between 25 and 70° Schoepper-Riegler, more preferably between 30° and 60° Schoepper-Riegler, and a paper binder.

According to another particular embodiment of the invention, said fibrous composition includes, as cellulose fibers, a fluff pulp.

Preferably, said fibrous sheet includes, on the surface, a reinforcing binder, in particular an acrylic-based polymer or a styrene-butadiene copolymer. Preferably, the amount of said binder is comprised between 10 and 35 g/m$^2$ by dry weight.

According to one particular embodiment of the invention, said material has been softened, especially (micro)creped or flexed.

Moreover, said material may include a sealant agent on at least one of its faces. It may include, on at least one of its faces, either a heat-sealable product, such as for example a microcrystalline wax, in particular a polyolefin wax, an EVA (ethylene/vinyl acetate)-type adhesive, an EAA (ethylene/acetic acid)-type adhesive, or a cold-sealable product, such as for example natural rubber.

According to one particular embodiment of the invention, the fibrous sheet of said material comprises an amount of polyamide fibers greater than 10% by weight relative to the total weight of fibers. In one particular embodiment of the invention, the polyamide fibers represent at least 15% by weight of the total weight in fibers of said fibrous composition.

According to another particular embodiment of the invention, the fibrous composition of said material may comprise, as fibers, essentially synthetic fibers, at least 50%, preferably at least 60% and even up to 100% of which are polyamide fibers, this material may therefore be suitable for gas, irradiation, steam, plasma or ozone sterilization processes.

Said material may be obtained using various known processes.

According to one particular embodiment, said material may be obtained by a wet process, of the paper type. It is possible to use a Fourdrinier paper machine, an inclined wire or cylinder-mold paper machine.

For example, it is possible to produce a sheet according to the invention on a paper machine with cellulose fibers, possibly modified like the rayon fibers coming from the sodium hydroxide treatment of viscose or regenerated cellulose fibers in a solvent a medium, such as those sold under the brand names Lyocell® or Tencel®, as a mixture with PA fibers and optionally with other synthetic fibers, such as polyethylene fiber pulp (PE pulp), all these fibers being bonded together either by thermal bonding or by water-jet bonding (i.e. hydroentangling) or chemically by means of the addition in bulk of a binder normally used in papermaking. In addition, a synthetic binder may be applied by a surface treatment using a size press or by spraying.

According to another particular method of manufacture, said material may be obtained by a dry process, which allows a nonwoven to be formed.

In particular, it is possible to manufacture a nonwoven of the SMS (spunbonded/meltblown/spunbonded) type, which is a multilayer sheet of synthetic fibers and filaments normally used in the field of synthetic materials for medical and hospital packagings. This nonwoven comprises in particular continuous polyamide fibers. If fluff pulp is used, the material is formed by a dry route, the fluff pulp and the PA fibers and, optionally other synthetic fibers, being able to be bonded by water jets.

In general, the fibers are bonded by known means, such as for example thermal bonding, water-jet bonding, and ultrasound.

During its manufacture, said material may be softened, especially by a dry treatment such as (micro)crimping or flexing, before being coated, where appropriate, with the sealant agent.

The invention also relates to sterilization packaging comprising a material as described above. This may be of any type of packaging: sachet, pouch, rigid container, tube, packaging sheet for hospital kits, blister pack, or else protective sheets for medical devices.

The invention will be more clearly understood with the aid of the following nonlimiting examples.

EXAMPLE 1

Comparative Example

A sheet was manufactured on a Fourdrinier paper machine in the following manner:

Cellulose fibers and PET (polyethylene terephthalate) synthetic fibers were suspended in an aqueous medium. The cellulose fibers were a mixture of long (resinous) fibers and short fibers, in a 3/2 ratio by weight, the fibers being refined to 58°SR. The PET fibers had a length of 6 mm and a linear density of 1.7 dtex. Added to this suspension were 0.26%, by dry weight of the total composition of the sheet, of a wet-strength agent of a PAE (polyamine epichlorohydrin) type and 1%, by dry weight of the total composition of the sheet, of a cationic starch as internal cohesion agent. This suspension was dewatered on the wire of the paper machine in order to form the sheet.

The sheet was impregnated in a size press with a synthetic binder (cohesion agent), a acrylic polymer used in the form of a stabilized aqueous suspension (commonly called latex). This acrylic binder was present in an amount of 18 g/m² by dry weight. The sheet was then dried at around 120° C. The sheet then had a grammage of 80 g/m².

EXAMPLES 2 TO 6

According to the Invention

The sheets were produced in the same method of manufacture as that of Example 1, the PET fibers being replaced with polyamide fibers.

EXAMPLE 7

A sheet comprising only synthetic fibers was produced. A pulp of polyethylene synthetic fibers (PE pulp having a binder role) was suspended in an aqueous medium, to which were added polyamide fibers having a length of 6 mm and a linear density of 1.7 dtex. A synthetic binder—a styrene-butadiene copolymer latex—was added in bulk in an amount of 30 g/m² by dry weight.

This suspension was dewatered on the wire of the machine in order to form the sheet. The sheet was dried at around 120° C. and then had a grammage of 80 g/m².

Data and Results of the Examples:

The data on the components of the sheets and the characteristics are given in Table 1.

Example 1, containing no polyamide fibers, had an initial tear strength of less than 1900 mN, whereas the other examples met the criteria of the invention.

Characterization Methods:

The sheets obtained according to the examples were characterized by the methods referenced below.

The measurements, except for the BFE, were made on specimens conditioned according to European Standard EN 20187 (equivalent to the standard ISO 187: 1995) in which the temperature was maintained at 230 and the relative humidity at 50%.

The grammage was determined according to International Standard ISO 536.

The mean initial tear strength (the mean of the measurements in the machine direction and in the transverse direction) was measured according to European Standard EN 21974, which corresponds to International Standard ISO 1974: 1990 (Elmendorf method).

The mean air permeability was measured according to the ISO 5636/3 standard (Bendtsen method).

The mean of the equivalent pores diameter was measured according to European Standard EN 868-3, Annex B.

The bacterial filtration efficiency BFE was determined according to the method published by the European Association EDANA under the reference 180.0-89 of February 1996.

TABLE 1

| | EXAMPLES | | | | | | |
|---|---|---|---|---|---|---|---|
| | Comparative Example 1 | Example 2 | Example 3 | Example 4 | Example 5 | Example 6 | Example 7 |
| Amount of cellulose fibers | 41 g/m² | 35 g/m² | 35 g/m² | 41 g/m² | 41 g/m² | 56 g/m² | 0 |
| Refining of the cellulose fibers (°SR) | 58 | 62 | 59 | 58 | 60 | 30 | / |
| Amount, nature-linear density, length of synthetic fibers | 21 g/m², PET, 1.7 dtex, 6 mm | 30 g/m², PA-6,6, 1.7 dtex, 6 mm | 30 g/m², PA-6,6, 1.7 dtex, 6 mm | 21 g/m², PA-6,6, 1.7 dtex, 6 mm | 21 g/m², 1.7 dtex, PA-6,6, 6 mm | 12 g/m², 1.7 dtex, PA-6,6, 6 mm | 30 g/m², PA-6,6, 1.7 dtex, 6 mm, 20 g/m² PE pulp |
| Dry amount and nature of the surface synthetic binder | 18 g/m², Primal E1845 acrylic polymer from Rhom & Haas | 15 g/m², Acronal LA471S acrylic polymer from BASF | 15 g/m², Acronal LA471S acrylic polymer from BASF | 18 g/m², Primal E1845 acrylic polymer from Rhom & Haas | 15 g/m², Latexia PE 1161 styrene-butadiene copolymer from Raisio | 12 g/m², Primal E1845 acrylic polymer from Rhom & Haas | 30 g/m², Latexia PE 1161 styrene-butadiene copolymer from Raisio |
| Dry amount of sealable wax | 0 | 0 | 0 | 0 | 3 g/m² | 0 | 20 g/m² |
| Grammage of material (g/m²) | 80 | 80 | 80 | 80 | 80 | 80 | 80 |
| Initial tear strength (mN) | 1855 | 4100 | 4300 | 2650 | 2350 | 1900 | 1920 |
| Bendtsen porosity(ml/min) | 700 | 800 | 900 | 660 | 550 | 240 | 400 |

TABLE 1-continued

| | EXAMPLES | | | | | | |
|---|---|---|---|---|---|---|---|
| | Comparative Example 1 | Example 2 | Example 3 | Example 4 | Example 5 | Example 6 | Example 7 |
| Maximum pore diameter (μm) | 26 | 24 | 26 | 25 | 22 | 18 | 17 |
| BFE (%) | 96% | 96% | 95% | 97% | 98% | 99.5% | 99% |
| Sterilization process compatibility | Gas, irradiation, steam | Gas, irradiation, steam | Gas, irradiation, steam | Gas, irradiation, steam | Gas, irradiation, steam | Gas, irradiation, steam | Gas, irradiation, plasma |
| Observations | Insufficient tear strength | | | | | | |

The invention claimed is:

1. A sterilization packaging material for medical devices awaiting sterilization, comprising a monolayer fibrous sheet comprising polyamide fibers, said monolayer fibrous sheet having a grammage of less than 100 g/m², measured according to international standard ISO 536, a mean initial tear strength, measured according to European Standard EN 21974, of 1900 mN or higher and a bacterial filtration efficiency (BFE) of 95% or higher.

2. The material as claimed in claim 1, wherein said monolayer fibrous sheet has a grammage of 90 g/m² or less, measured according to the international standard ISO 536.

3. The material as claimed in claim 1, wherein the polyamide fibers are chosen from polyamide-6 and polyamide-6,6 fibers.

4. The material as claimed in claim 1, wherein said polyamide fibers have a length of 5 mm or greater.

5. The material as claimed in claim 1, wherein said polyamide fibers have a mean linear density greater than 1.5 dtex.

6. The material as claimed in claim 1, wherein said polyamide fibers include antioxidants giving them irradiation resistance.

7. The material as claimed in claim 1, wherein said polyamide fibers are chopped fibers.

8. The material as claimed in claim 1, wherein said fibrous sheet includes, in bulk, cellulose fibers, refined to between 25 and 70° Schoepper-Riegler, and a paper binder.

9. The material as claimed in claim 1, wherein said fibrous sheet includes, as cellulose fibers, a fluff pulp.

10. The material as claimed in claim 1, wherein said fibrous sheet comprises an amount of polyamide fibers of greater than 10% by weight, relative to the total weight of fibers.

11. The material as claimed in claim 1, wherein said fibrous sheet comprises only synthetic fibers.

12. The material as claimed in claim 11, wherein the synthetic fibers comprise at least 50% of polyamide fibers.

13. The material as claimed in claim 11, wherein the synthetic fibers comprise at least 60% of polyamide fibers.

14. The material as claimed in claim 1, wherein said fibrous sheet includes, on the surface, a binder.

15. The material as claimed in claim 14, wherein the amount of said binder is between 10 and 35 g/m² by dry weight.

16. The material as claimed in claim 14, wherein the binder includes at least one of an acrylic-based polymer binder and a styrene-butadiene copolymer.

17. The material as claimed in claim 1, wherein the material has been softened.

18. The material as claimed in claim 17, wherein the material has been at least one of (micro) crimped or flexed.

19. The material as claimed in claim 1, wherein the material includes a sealant agent on at least one of its faces.

20. A sterilization package comprising material as claimed in claim 1.

21. The material as claimed in claim 1, wherein said fibrous sheet comprises an amount of polyamide fibers of greater than 15% by weight relative to the total weight of fibers.

22. The material as claimed in claim 1, wherein said monolayer fibrous sheet has a grammage between 40 and 80 g/m², measured according to the international standard ISO 536.

* * * * *